US008574510B2

(12) United States Patent
Gofman et al.

(10) Patent No.: US 8,574,510 B2
(45) Date of Patent: Nov. 5, 2013

(54) STACKABLE ELECTROCHEMICAL ANALYTE SENSORS, SYSTEMS AND METHODS INCLUDING SAME

(75) Inventors: Igor Gofman, Croton-on-Hudson, NY (US); Robert S. Sams, Peekskill, NY (US)

(73) Assignee: Bayer Healthcare LLC, Tarrytown, NY (US)

( * ) Notice: Subject to any disclaimer, the term of this patent is extended or adjusted under 35 U.S.C. 154(b) by 319 days.

(21) Appl. No.: 12/893,067

(22) Filed: Sep. 29, 2010

(65) Prior Publication Data

US 2011/0073476 A1     Mar. 31, 2011

Related U.S. Application Data

(60) Provisional application No. 61/247,031, filed on Sep. 30, 2009.

(51) Int. Cl.
*G01N 27/26* (2006.01)
(52) U.S. Cl.
USPC ........... 422/401; 422/402; 422/403; 422/404; 422/405; 422/560; 422/561; 422/565; 422/417; 422/430; 422/68.1; 422/69; 422/82.01; 422/82.02; 422/82.03; 422/82.04; 422/82.05; 422/82.06; 422/82.07; 422/82.08; 422/82.09; 422/82.11; 221/34; 221/36; 221/37; 221/40; 221/41; 221/42; 221/45; 221/46; 221/56; 221/57; 221/58; 221/59; 221/60; 221/67; 221/177; 221/129; 204/403.01; 204/403.02; 204/402.03; 204/403.04; 204/403.05; 222/23; 222/522; 222/523; 222/524; 222/525; 222/575; 435/317.1; 436/183

(58) Field of Classification Search
USPC ......... 422/401–405, 560, 561, 565, 417, 430, 422/68.1, 69, 82.01–82.11, 83, 86, 87–92, 422/557; 221/34, 36, 37, 40–42, 45, 46, 221/56–60, 67, 177, 129; 204/403.1–403.15; 222/23, 522–525, 222/575; 435/317.1; 436/183
See application file for complete search history.

(56) References Cited

U.S. PATENT DOCUMENTS

| | | | |
|---|---|---|---|
| 3,592,356 A * | 7/1971 | Rovin | 221/36 |
| 4,721,677 A | 1/1988 | Clark | |
| 5,335,816 A * | 8/1994 | Kaufman et al. | 221/13 |
| 5,335,822 A * | 8/1994 | Kasper | 221/259 |
| 5,609,823 A * | 3/1997 | Harttig et al. | 422/66 |
| 5,846,486 A | 12/1998 | Pugh | |
| 5,856,195 A | 1/1999 | Charlton | |
| 6,036,924 A | 3/2000 | Simmons | |
| 6,099,802 A | 8/2000 | Pugh | |
| 6,170,230 B1 * | 1/2001 | Chudy et al. | 53/168 |
| 6,625,952 B1 * | 9/2003 | Chudy et al. | 53/168 |

(Continued)

*Primary Examiner* — Jill Warden
*Assistant Examiner* — Shogo Sasaki
(74) *Attorney, Agent, or Firm* — Dugan & Dugan, PC

(57) ABSTRACT

In some aspects, an analyte sensor is provided for detecting an analyte concentration level in a bio-fluid sample. The analyte sensor has a base with first and second ends, a concave recess in the first end, a second end receiving surface, and a sidewall extending between the ends. An electrode may be provided on the receiving surface with an electrochemically-active region coupled to the electrode. A conductor in electrical contact with the electrode may extend along the sidewall and may be adapted to be in electrical contact with a first contact of an analyte meter. Manufacturing methods and systems utilizing and dispensing the analyte sensors are provided, as are numerous other aspects.

6 Claims, 12 Drawing Sheets

(56) References Cited

U.S. PATENT DOCUMENTS

| | | |
|---|---|---|
| 6,827,899 B2 | 12/2004 | Maisey |
| 6,908,008 B2 * | 6/2005 | Pugh .............................. 221/135 |
| 6,997,343 B2 | 2/2006 | May |
| 7,138,089 B2 | 11/2006 | Aitken |
| 7,264,139 B2 * | 9/2007 | Brickwood et al. .......... 221/270 |
| 7,270,247 B2 | 9/2007 | Charlton |
| 7,552,843 B2 * | 6/2009 | Kuriger et al. ................ 221/228 |
| 2002/0057993 A1 * | 5/2002 | Maisey et al. .............. 422/82.01 |
| 2002/0076349 A1 * | 6/2002 | Aitken et al. .................... 422/58 |
| 2003/0089730 A1 * | 5/2003 | May et al. ..................... 221/232 |
| 2003/0116583 A1 * | 6/2003 | Pugh .............................. 221/268 |
| 2003/0175155 A1 * | 9/2003 | Charlton ......................... 422/61 |
| 2003/0191415 A1 * | 10/2003 | Moerman et al. ............. 600/584 |
| 2003/0223906 A1 | 12/2003 | McAllister |
| 2004/0178216 A1 * | 9/2004 | Brickwood et al. .......... 221/268 |
| 2006/0076358 A1 * | 4/2006 | Shigeyama et al. ........... 221/104 |
| 2007/0189928 A1 | 8/2007 | Sabol |
| 2007/0196240 A1 | 8/2007 | Boozer |
| 2008/0094804 A1 * | 4/2008 | Reynolds et al. .............. 361/727 |
| 2008/0131322 A1 | 6/2008 | Kheiri |
| 2008/0164280 A1 * | 7/2008 | Kuriger et al. ................ 221/135 |
| 2008/0181818 A1 * | 7/2008 | Ruan ............................ 422/68.1 |

\* cited by examiner

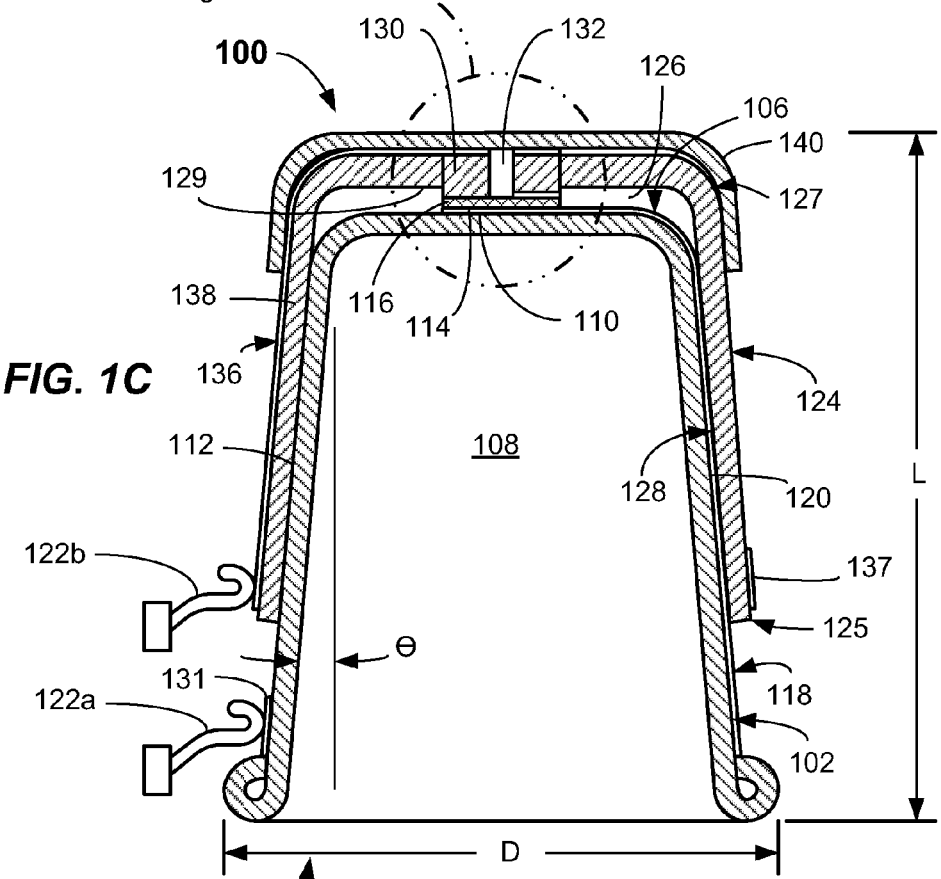
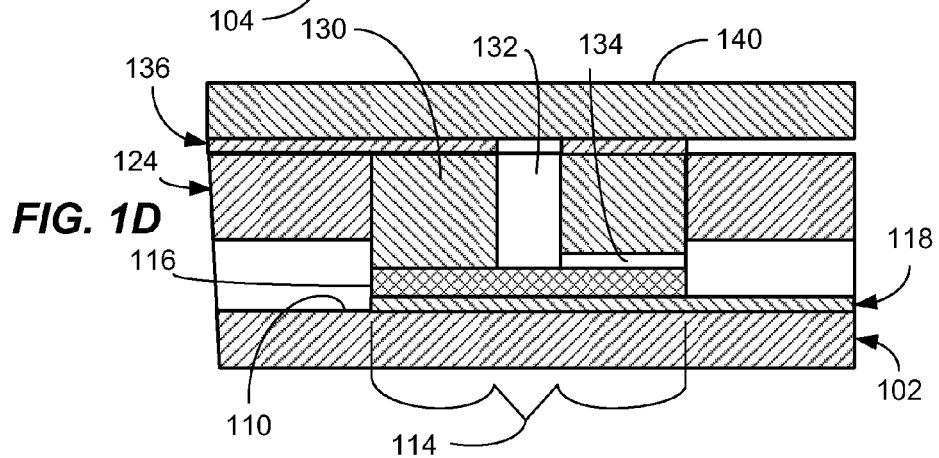

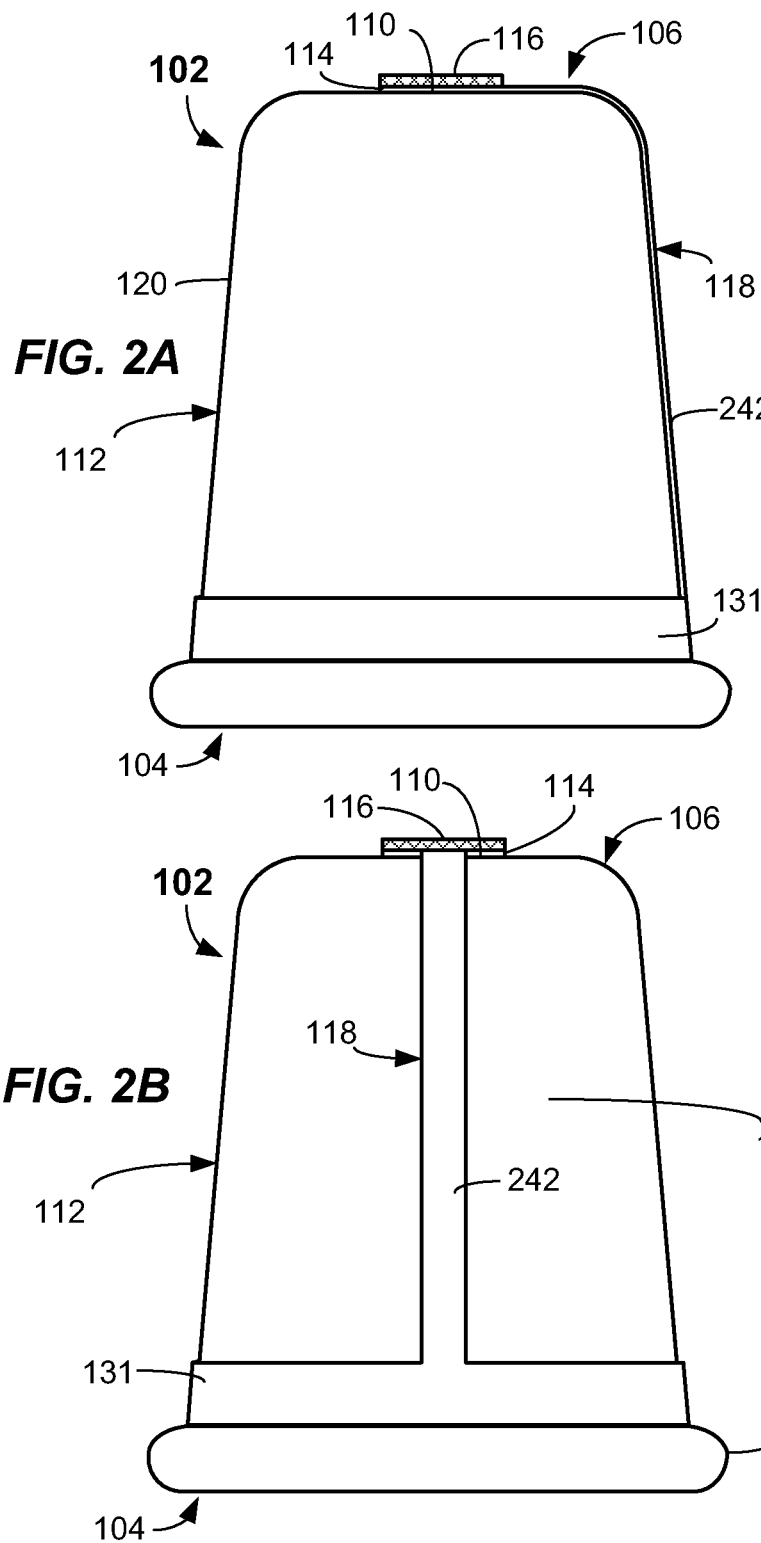

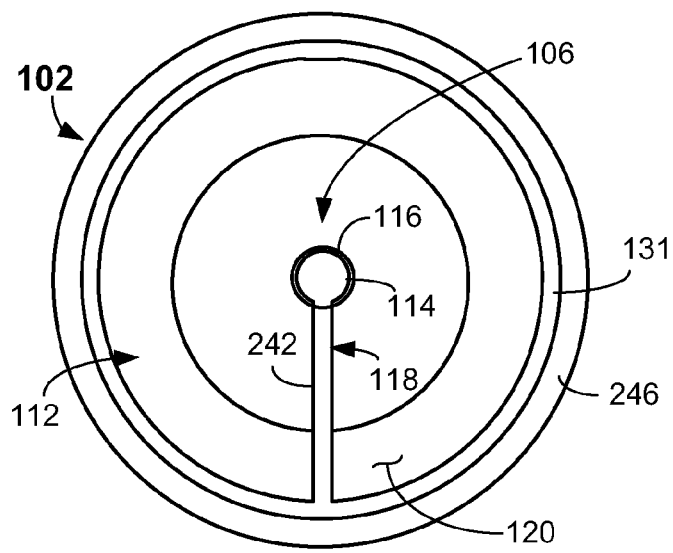
FIG. 2C
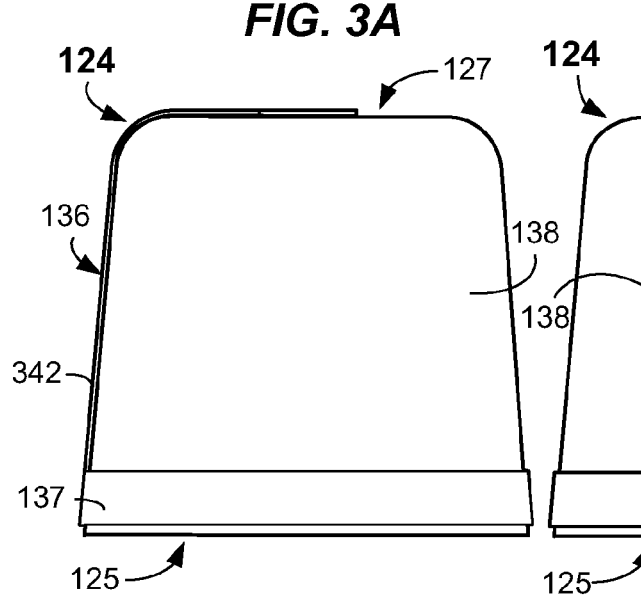
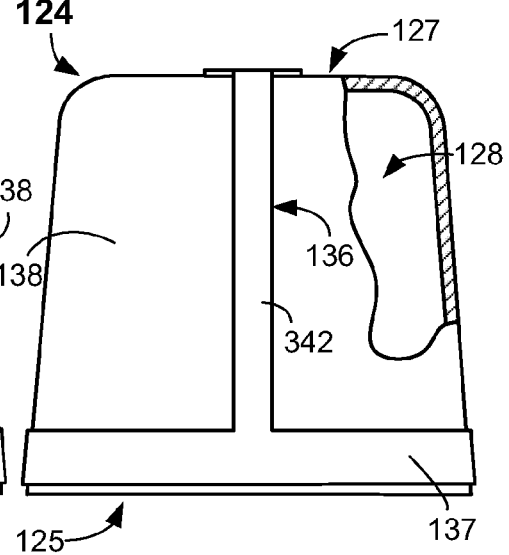

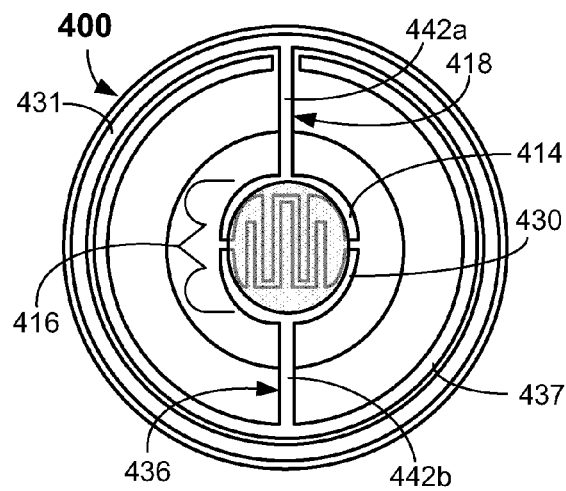
FIG. 4A
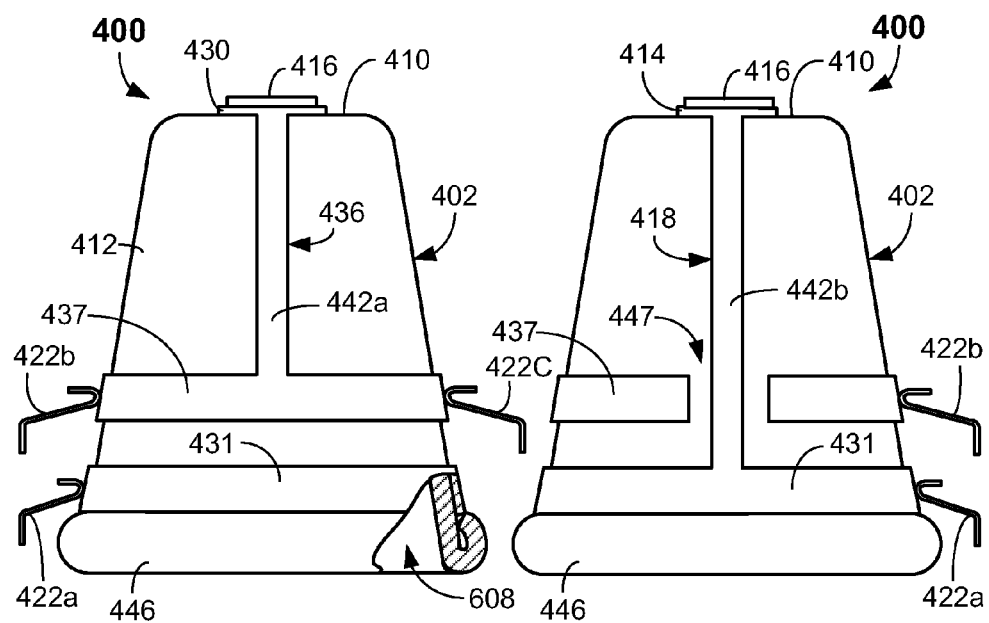
FIG. 4B    FIG. 4C

STACKABLE ELECTROCHEMICAL ANALYTE SENSORS, SYSTEMS AND METHODS INCLUDING SAME

RELATED APPLICATIONS

This application claims priority to U.S. Provisional Application Ser. No. 61/247,031 entitled "STACKABLE ELECTROCHEMICAL ANALYTE SENSORS, SYSTEMS AND METHODS INCLUDING SAME" filed on Sep. 30, 2009, the disclosure of which is hereby incorporated by reference in its entirety herein.

FIELD OF THE INVENTION

The present invention relates to electrochemical analyte sensors that may be used to detect an analyte concentration level in a bio-fluid sample, systems including the analyte sensors, and methods of manufacturing thereof.

BACKGROUND OF THE INVENTION

The monitoring of analyte concentration levels in a bio-fluid may be an important part of health diagnostics. For example, an electrochemical analyte sensor may be employed for monitoring of a patient's blood glucose level as part of diabetes treatment and care. Furthermore, analyte sensors may be used to measure other analytes, such as lactate, keytones, total cholesterol, uric acid, lipids, triglycerides, high density lipoprotein (HDL), low density lipoprotein (LDL), hemoglobin A1c, etc.

An electrochemical analyte sensor may be employed, for instance, by detecting an analyte concentration level in a bio-fluid sample such as from a single sample of blood or other interstitial fluid. For example, the bio-fluid may be obtained from the patient via a lancet (e.g., by a pinprick or needle). Typically, after a bio-fluid sample has been obtained from the patient, such as by the use of a lancet, the sample may then be transferred to a medium (e.g., a test strip analyte sensor or a detector) for measurement of the bio-fluid sample's analyte concentration level.

Because conventional electrochemical analyte sensors may be provided in the form of a strip, for example, it may be difficult to package the sensors in a small packaging volume. Accordingly, it may be beneficial to provide an analyte sensor adapted for bio-fluid analyte sampling that may be suitably packaged in a small volume and more easily dispensed.

SUMMARY OF THE INVENTION

In a first aspect, the present invention provides an analyte sensor including a base having a first end and a second end opposite from the first end, a concave recess formed in the first end, a receiving surface on the second end, and a sidewall extending between the first end and the second end; a first electrode provided proximate to the receiving surface; an electrochemically-active region electrically coupled with at least the first electrode; and a first conductor in electrical contact with the first electrode and extending along the sidewall, the first conductor adapted to be in electrical contact with a first contact of an analyte meter.

In another aspect, the present invention provides an analyte sensor adapted to detect an analyte concentration level in a bio-fluid sample, including a base having a first end and a second end and a sidewall extending between the first end and the second end, the first end including a concave recess and the second end including a receiving surface; a first electrode and a second electrode provided on the receiving surface; an active region positioned in contact with the first electrode and the second electrode; and a first conductor and a second conductor electrically coupled to the first and second electrodes, respectively, the first conductor including a contact portion adapted to be in electrical contact with a first contact of an analyte meter, and the second conductor including a contact portion adapted to be in electrical contact with a second contact of the analyte meter.

In yet another aspect, the present invention provides an analyte sensor dispenser system, including a dispenser body having a channel extending in the dispenser body; a plurality of analyte sensors provided in a stacked configuration within the channel, each analyte sensor including at least one conductor; an advancer coupled to at least one of the plurality of analyte sensors; a port from which individual analyte sensors of the plurality of analyte sensors are adapted to be incrementally dispensable; and an electrical contact in the port adapted to contact the at least one conductor.

In yet another aspect, the present invention provides an analyte sensor dispenser cartridge, including a cartridge body having a channel extending in the cartridge body, the cartridge body adapted to be received in an analyte meter; a plurality of analyte sensors provided in a stacked configuration within the channel, each analyte sensor including conductive contacting portions on a surface thereof; and electrical contacts provided in the channel and in electrical contact with conductive contacting portions of an end one of the plurality of analyte sensors as provided in the stacked configuration.

In a method aspect, the present invention provides a method of manufacturing an analyte sensor including providing a base having a first end and a second end and a sidewall extending between the first end and the second end, the first end including a concave opening and the second end including a receiving surface; forming a first electrode on the receiving surface; applying an active region in contact with the first electrode; and providing a conductor in electrical contact with the electrode and extending along an outer surface of the sidewall, the conductor including a contact portion adapted to be in electrical contact with a first electrical contact of an analyte meter.

Other features and aspects of the present invention will become more fully apparent from the following detailed description, the appended claims and the accompanying drawings.

BRIEF DESCRIPTION OF THE DRAWINGS

FIG. 1C is a cross-sectioned side view of an exemplary embodiment of an analyte sensor of FIG. 1A taken along section line "1C-1C."

FIG. 1D is an enlarged cross-sectioned view of a portion of an exemplary embodiment of an analyte sensor of FIG. 1C.

FIGS. 2A-2B are two side views of an exemplary embodiment of a base of the analyte sensor of FIG. 1A.

FIG. 2C is a top view of an exemplary embodiment of a base of the analyte sensor of FIG. 1A.

FIGS. 3A-3B are two side views of an exemplary embodiment of a second member of the analyte sensor of FIG. 1A.

FIGS. 4A-4C are respective top and side views of another exemplary embodiment of an analyte sensor according to the present invention.

DETAILED DESCRIPTION

Figure 1A:
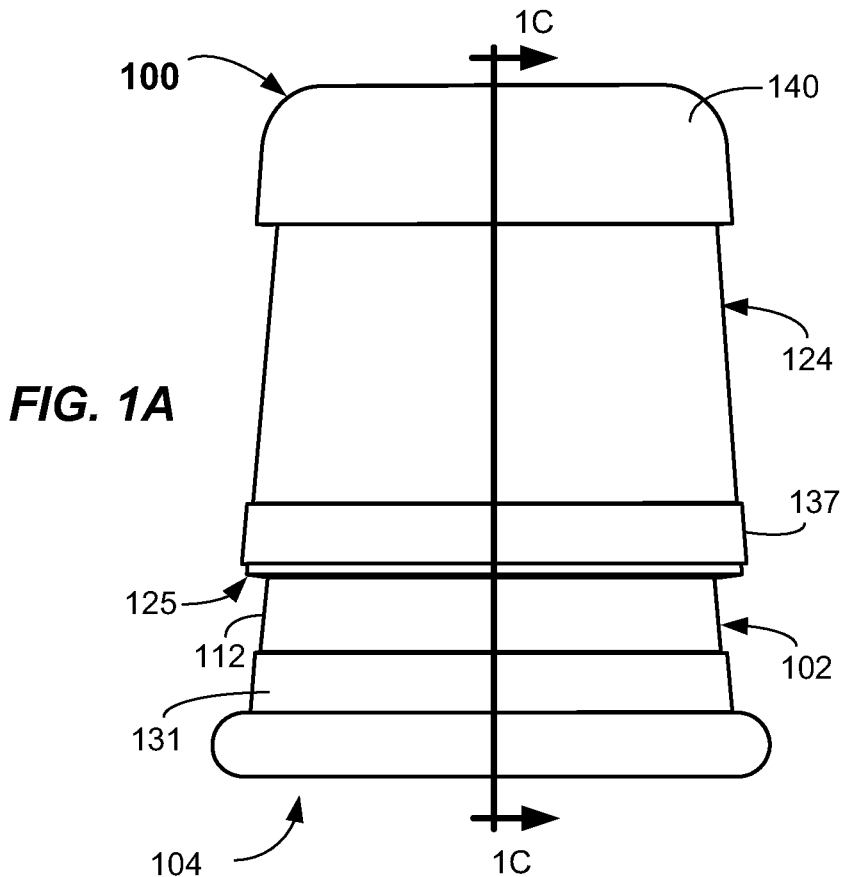
FIG. 1A is a side view of an exemplary embodiment of an analyte sensor provided according to the present invention.
Figure 1B:
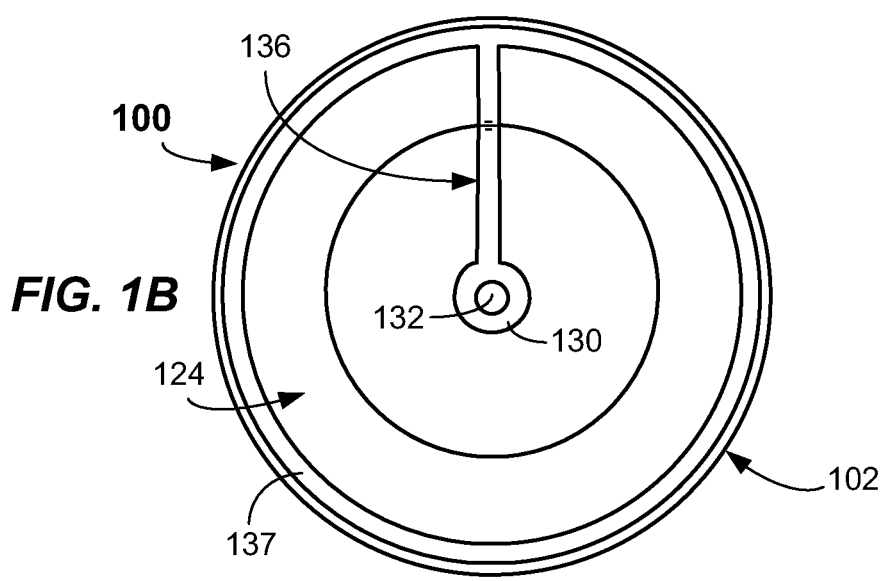
FIG. 1B is a top view of an exemplary embodiment of an analyte sensor of FIG. 1A with the cap 140 removed for clarity.

According to some aspects of the present invention, an analyte sensor is provided. The analyte sensor may include a cup-shaped configuration which allows the analyte sensors to be stacked, one atop of another, in a compact configuration which may allow the analyte sensors to be housed in a relatively small space.

In some embodiments, the analyte sensor may include a base with a concave recess, a receiving surface, and a sidewall which may have a frustoconical shape. The base may include a first electrode provided proximate to the receiving surface, and an electrochemically-active region (of any suitable analyte detection chemistry) electrically coupled to the first electrode. A first conductor is electrically coupled with the first electrode and may extend along the sidewall. The first conductor may include a contact portion formed of an annular ring extending in a radial direction at least partially around the sidewall. The first conductor is adapted to be in electrical contact with a first electrical contact of an analyte meter. Accordingly, the user may apply a bio-fluid sample to the active region and the analyte meter may display a reading thereof.

In other embodiments, an analyte sensor dispenser system is provided. The analyte sensor dispenser includes a dispenser body having a channel extending within the dispenser body and a plurality of analyte sensors may be provided in a stacked configuration within the channel. An advancer may be coupled to the stack of analyte sensors in the channel so that individual analyte sensors may be incrementally advanced and dispensed from a port of the analyte sensor dispenser system. Each of the analyte sensors dispensed includes an electrical conductor, which is adapted to contact an electrical contact of the dispenser system wherein the conductor may be provided in the port or in a cartridge assembly received in the meter. In some embodiments, the analyte sensor is appropriately positioned and electrically connected to the analyte meter as it is being dispensed so that an analyte reading may be accomplished as the analyte sensor is positioned in the port.

These and other embodiments of analyte sensors, systems including the analyte sensors and methods for manufacturing the analyte sensors are described below with reference to FIGS. 1A-9.

FIGS. 1A-1D show various views of a first exemplary embodiment of an analyte sensor 100 provided according to the present invention. The analyte sensor 100 may include a base 102 preferably formed of an insulating material. The base 102 may have a first end 104 and a second end 106 (FIG. 1C) opposite the first end 104 and spaced therefrom. Further, the base 102 may include a concave recess 108 (FIG. 1C) formed into the first end 104, a receiving surface 110 formed on the second end, and a sidewall 112 extending between the first end 104 and the second end 106. The base 102 may have a cup-shaped configuration. The concave recess 108 may extend along an axial length of the analyte sensor 100 and terminate a distance away from the first end 104. The side wall 112 may, in some embodiments, be constructed as a frustoconical surface which may include an included acute draft angle (ø) of between about 10 degrees and 45 degrees of the sidewall 112, or even between about 10 and 30 degrees, and in some embodiments about 20 degrees. Other draft angles (ø) may be used. Further, in some embodiments, the receiving surface 110 may be a planar surface, for example. Other shapes of the sidewall 112 and shapes of the receiving surface 110 may be used. However, the sidewall shape should allow the various analyte sensors 100 to be provided in a stacked relationship, one on top of the next in a compact configuration. The base 102 may be manufactured from of a polymer material, such as a polycarbonate, polyethylene terephthalate, polyimide, high density polyethylene, or polystyrene material, for example, and may be stamped out or thermally formed or molded, for example.

Additionally, a first electrode 114 may be provided proximate the receiving surface 110 and an electrochemically-active region 116 may be provided on the first electrode such that there is an electrical coupling with the first electrode 114. A first conductor 118 may be provided in electrical contact with the first electrode 114 and may extend along an outer surface 120 of the sidewall 112. The first conductor 118 is adapted to be in electrical contact with a first electrical contact 122a of an analyte meter (meter not shown in FIG. 1A-1D). The first electrode 114 and first conductor 118 may be made from any suitable electrically-conductive material. Suitable materials include carbon, graphite, gold, silver, palladium or platinum, carbon/graphite PTF, silver/silver chloride or an electrically-conductive ink such as a carbon and silver-containing ink. Other suitable conductive materials may be used.

The electrochemically-active region 116 may be applied onto the first electrode 114 or otherwise electrically coupled thereto. Briefly, however, the electrochemically-active region 116 may be adapted to be exposed to the bio-fluid sample. The electrochemically-active region 116 may include one or more catalytic agents or reagents adapted to promote an electrochemical reaction between an analyte in the bio-fluid sample and the catalytic agents or reagents included in the electrochemically-active region 116, or otherwise generate an electrical current upon being exposed to the bio-fluid sample. The mobile electrons produced may be conducted to the analyte meter (FIGS. 4D, 5A-5B and 6A-6C), for example, by the first electrode 114 and the first conductor 118.

One group of catalytic agents useful for providing the electrochemically-active region 116 may be the class of oxidase enzymes which includes, for example, glucose oxidase (which converts glucose), lactate oxidase (which converts lactate), and D-aspartate oxidase (which converts D-aspartate and D-glutamate). In embodiments in which glucose is the analyte of interest, glucose dehydrogenase (GDH) may optionally be used. Pyrolloquinoline quinine (PQQ) or flavin adenine dinucleotide (FAD) dependent may also be used. A more detailed list of oxidase enzymes which may be employed in the present invention is provided in U.S. Pat. No. 4,721,677, entitled "Implantable Gas-containing Biosensor and Method for Measuring an Analyte such as Glucose" to Clark Jr. which is hereby incorporated by reference herein in its entirety. Catalytic enzymes other than oxidase enzymes may also be used.

The electrochemically-active region 116 may include one or more layers (not explicitly shown) in which the catalytic agents (e.g., enzymes) and/or other reagents may be immobilized or deposited. The one or more layers may comprise various polymers, for example, including silicone-based or organic polymers such as polyvinylpyrrolidone, polyvinylalcohol, polyethylene oxide, cellulosic polymers such as hydroxyethylcellulose or carboxymethyl cellulose, polyethylenes, polyurethanes, polypropylenes, polyterafluoroethylenes, block co-polymers, sol-gels, etc. A number of different techniques may be used to immobilize the enzymes in the one or more layers in the electrochemically-active region 116 including, but not limited to, coupling the enzymes to the lattice of a polymer matrix such as a sol gel, cross-linking the agents to a suitable matrix such as glutaraldehyde, electropolymerization, and formation of an array between the enzymes via covalent binding, or the like.

In some embodiments, an electrochemically-active layer may form the electrode or be deposited on the first electrode. The electrochemically-active layer may include, for example, noble metals such as platinum, palladium, gold or rhodium, or other suitable materials. In a glucose detection embodiment, the electrochemically-active layer may undergo a redox reaction with hydrogen peroxide when polarized appropriately. The redox reaction may cause an electrical current to be generated by electron transfer that is proportional to the concentration of the analyte that has been converted into hydrogen peroxide. This current may be conducted and conveyed from the electrochemically-active layer through the first conductor 118 to an analyte testing system (e.g., an analyte meter).

In some embodiments, a mediator may be included within the electrochemically-active region 116 to promote the conversion of the analyte to detectable reaction products. Mediators comprise substances that act as intermediaries between the catalytic agent and the first electrode 114. For example, a mediator may promote electron transfer between the reaction center where catalytic breakdown of an analyte takes place and the first electrode. Suitable mediators may include one or more of the following: metal complexes including ferrocene and its derivatives, ferrocyanide, phenothiazine derivatives, osmium complexes, quinines, phthalocyanines, organic dyes as well as other substances. In some embodiments, the mediators may be cross-linked along with catalytic agents directly to the first electrode 114.

According to some embodiments of the invention, a second member 124 may be provided. A stacking end 125 including a concave recess 128 of the second member 124 may be received over the second end 106 of the base 102. The second member 124 may be sized so that a snug fit is provided between the base 102 and the second member 124. The second member 124 may be suitably adhered, fused or mechanically fastened to the base 102 by an adhesive and/or heat and pressure and/or interfering members (e.g., a snap fit). The assembly operation may form a space 126 between the respective receiving surface 110 of the base 102 and an inner surface 129 of the second member 124 at a second end 127 of the second member 124. As installed, a conductive electrode portion 130 may extend into the concave recess 128 such that it may be provided in electrical contact with the electrochemically-active region 116 upon assembly. The conductive electrode portion 130 may function as a reference electrode and/or counter electrode, for example. The conductive electrode portion 130 may be annularly shaped and may include a cavity 132 formed therein which extends from the terminal end of the second member 124 to the electrochemically-active region 116.

The cavity 132 may be circular in cross-section and may be adapted to receive a bio-fluid sample inserted through an open end thereof, for example. In particular, the cavity 132 may be at least partially formed and defined, for example, by inner surfaces of the conductive electrode portion 130 and an upper surface of the electrochemically-active region 116. The cavity 132 may have any shape, but preferably a shape which promotes capillary action to cause a droplet of bio-fluid to be drawn into the cavity 132 when applied to the entrance of the cavity 132 by a user. The bio-fluid sample may be drawn into the cavity 132 and come into intimate contact with the electrochemically-active region 116. A vent 134 (FIG. 1D), such as a hole or port, may be provided to assist capillary action. In the embodiment shown, the vent 134 may be a groove or slot formed into a bottom portion of the conductive electrode portion 130. The cavity 132 may have a length of about 2-5 mm and a width of about 0.5 to 1.5 mm, for example. Other dimensions may be used.

A second conductor 136 may be provided in electrical contact with the conductive electrode portion 130. For example, the second conductor 136 may extend from an end of the second member 124 alongside a second sidewall 138 of the second member 124. The second conductor 136 may include a contacting portion 137 that is adapted to be contacted by a second electrical contact 122b of an analyte meter system (See FIGS. 1C, 4D, 5C and 9).

In some embodiments, a cap 140 may be provided over the entry end 127 of the second member 124. The cap 140 may serve to seal against the second member 124 to limit environmental exposure to the active region 116. As shown in FIG. 1C, the analyte sensor 100 may include a length (L) of between about 5 mm and 40 mm, or even between about 15 mm and 25 mm, and in some embodiments about 20 mm. The analyte sensor 100 may include a maximum diameter (D) of between about 5 mm and 15 mm, or even between about 5 mm and 10 mm, and in some embodiments about 5 mm. Other length (L) and diameter (D) dimensions may be used.

Figure 5A:
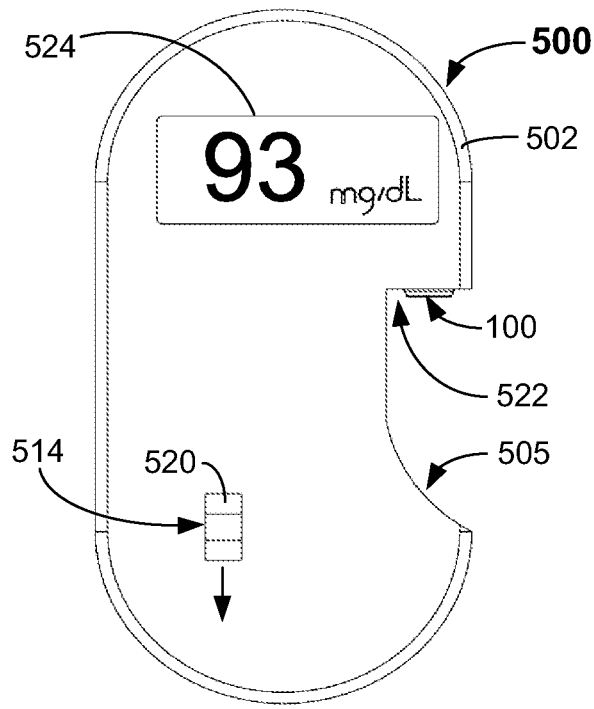
FIG. 5A is a frontal view of an analyte sensor dispenser system adapted to dispense an exemplary embodiment of an analyte sensor according to an embodiment of the present invention.
Figure 5B:
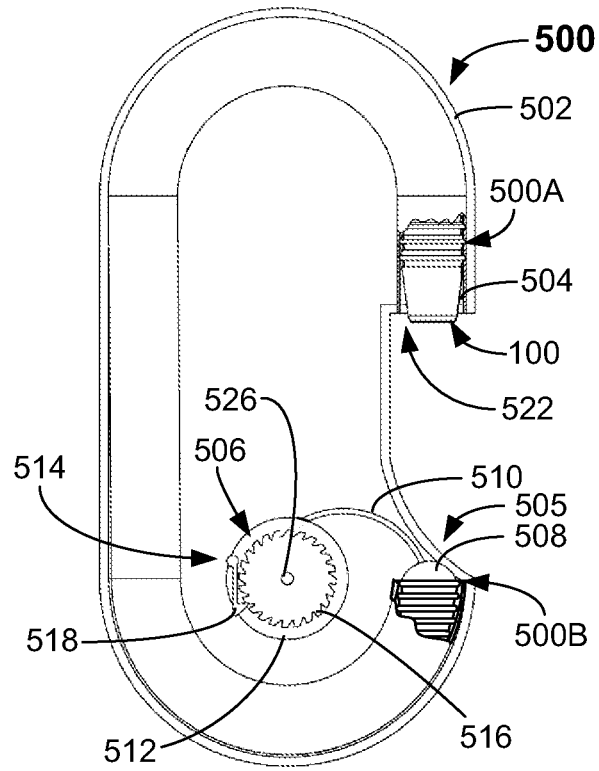
FIG. 5B is a partial cutout view of an inside of the analyte sensor dispenser system of FIG. 5A.
Figure 6A:
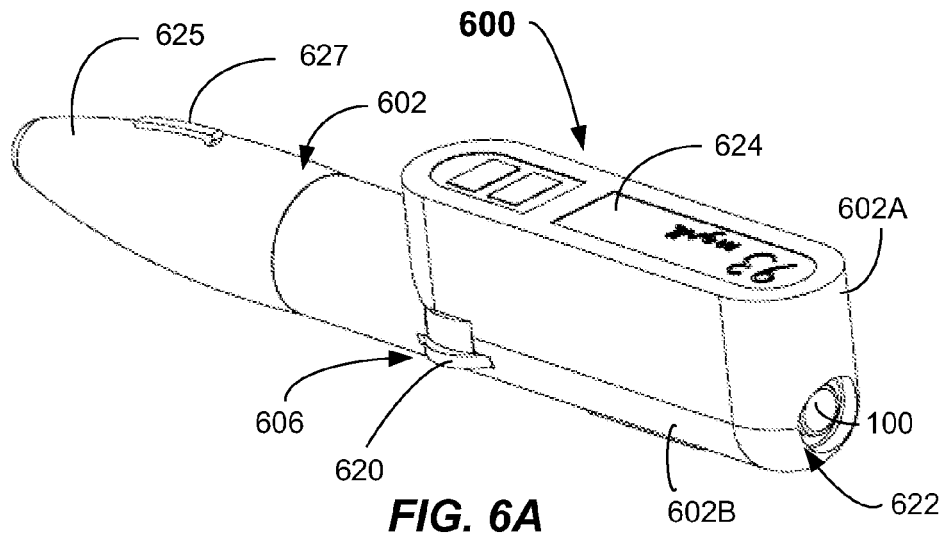
FIG. 6A is an isometric view of another embodiment of analyte sensor dispenser apparatus adapted to dispense an exemplary embodiment of an analyte sensor according to the present invention.

In operation, upon insertion of a droplet of bio-fluid into the cavity 132 such that it comes into contact with the electrochemically-active region 116, an electrical current may be generated which may be proportional to the concentration of the analyte in the bio-fluid sample. This electrical current may then be conducted by an electrical circuit including the first and second conductors 118, 136 and the electrical contacts 122a, 122b, and may be appropriately conditioned and displayed in any suitable readout form, such as in a digital readout of an analyte meter system (e.g., a blood glucose meter) as shown in FIGS. 5A-5B and 6A.

As further shown in FIGS. 2A-2C, an embodiment of the base 102 is shown. The depicted embodiment illustrates the first conductor 118 being made up of a connecting portion 242 and a contacting portion 131. The connecting portion 242 extends from the first electrode 114 on the receiving surface 110 (underneath the electrochemically-active region 116) on the second end 106, along the outer surface 120 of the sidewall 112 of the base 102 and electrically connects the first electrode 114 and the contacting portion 131 at the first end 104. The contacting portion 131 may extend radially, at least partially, or, in this embodiment, fully about the periphery of the sidewall 112 of the base 102 thereby forming an annular ring surrounding the base 102. As will be apparent from other embodiments described herein, the annular ring may include a break therein at one point around its periphery. The contacting portion 131 may be positioned proximate the first end 104 of the base 102 and located adjacent to a lip 246 formed on the base 102. The lip 246 may be provided to enable ease of stacking and/or removal of one analyte sensor over another. Moreover, the lip 246 may be formed and provided to enable sealing of one analyte sensor relative to the next in stacked relationship, so that environmental exposure of the electrochemically-active region 116 may be minimized. Furthermore, the lips may aid in a detent feature to be described more fully herein below.

As shown in FIGS. 3A and 3B, the second member 124 may also include a second conductor 136 which may function as a portion of a reference electrode providing a path (e.g., a return path) for an electrical current generated by the analyte sensor 100 (FIG. 1A). In one or more embodiments, the second conductor 136 may function as a counter electrode. The second conductor 136 may, similar to the first conductor 118 (FIGS. 2A-2B), include a connecting portion 342 and the contacting portion 137. The connecting portion 342 may extend alongside the second sidewall 138 of the second member 124 between a stacking end 125 and an entry end 127 of the second member 124. The connecting portion 342 may connect between the conductive contacting portion 131 (FIG. 1C-1D) at the entry end 127 and the contacted portion 137 located proximate the stacking end 125.

The first electrode 114 and first and second conductors 118, 136 may comprise any suitable electrically-conductive material, such as the conductive materials described above. In a preferred implementation, the conductors 118, 136 may be printed on the base 102 and the second member 124 with conductive ink by an ink jet process, for example. However, they may take on other forms of conductive materials (e.g., a wire, foil, strip, or film). The concave recess 128 of the second member 124 is adapted to be received over the second end 106 of the base 102.

Figure 4D:
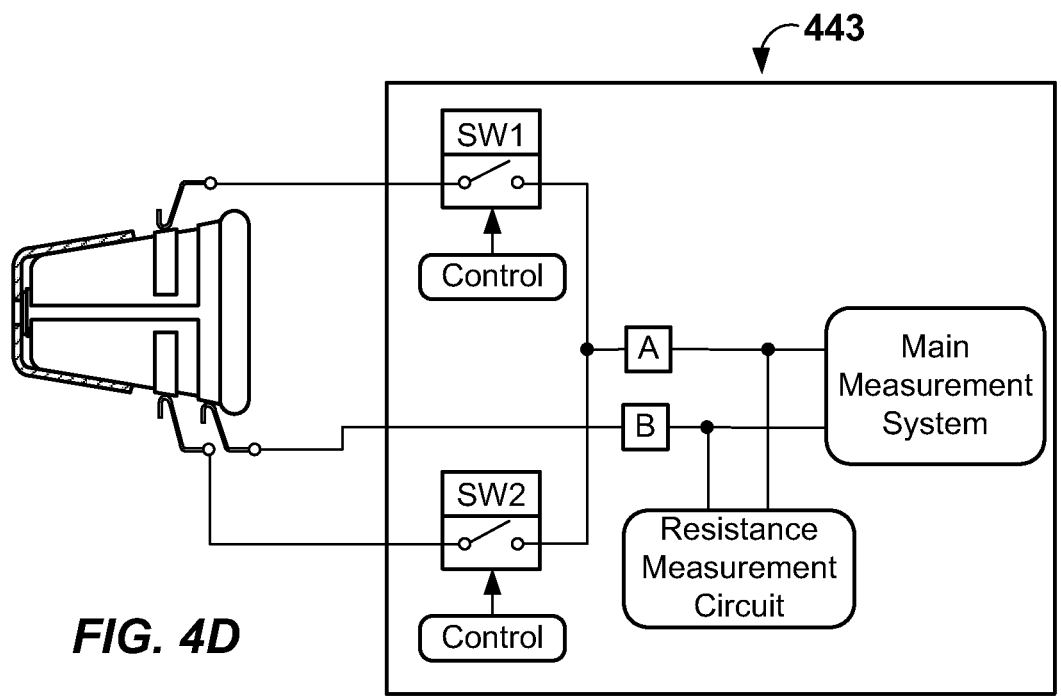
FIG. 4D is a schematic diagram of an exemplary embodiment of an electrical circuit adapted to interface with an analyte sensor according to the present invention.

FIGS. 4A-4C describe an exemplary alternative embodiment of an analyte sensor 400 according to the invention. The structure of the analyte sensor 400 is similar to the aforementioned embodiments, i.e., it may have a cup shape or thimble shape, which is stackable. However, in this embodiment, the base 402 includes both a first conductor 418 and a second conductor 436 formed thereon. The second member 424 (FIG. 4E) is not shown in FIGS. 4A-4C for clarity. Electrodes 414, 430 may be formed on a receiving surface 410 and may include interleaved electrode fingers, which may form multiple gaps, and an electrochemically-active region 416, as before described, may be applied over the electrodes 414, 430. As in all embodiments described herein, a mask may be used for precise control and application of an applied area of the electrochemically-active region 416. First and second conductors 418, 436 may include contacting portions 431, 437 and connecting portions 442a, 442b, respectively. The conductors 418, 436 provide the electrical path for an electrical connection between the electrodes 414 and 430 and electrical contacts 422a, 422b, 422c of a suitable analyte meter (See FIGS. 4D, 5A-5C, 6, and 9). In the present embodiment, the contacting portion 431 may be formed in the shape of an unbroken annular ring encircling a lower periphery of the sidewall 412 adjacent to the lip 446. The contacting portion 437 of the second conductor 436 may be formed as a broken annular ring, which may radially encircle the sidewall 412 at a position, axially spaced from the contacting portion 431. As should be recognized, the electrical contact 422a may make positive electrical contact with the contacting portion 431 regardless of the rotational orientation of the analyte sensor 400 relative to the contact 422a.

In the case of the contact 422b, positive electrical contact may be made for almost the entire radial extent (Case 1), except at the gap 447 where the connecting portion 442b passes through. In another case, the orientation may result in the contact 422b, for example, being in electrical contact with the connecting portion 442b at the gap 447 (Case 2). A further condition may occur when the contact 422b resides in the gap 447, but not in contact with either the contacting portion 437 or the connecting portion 442b (Case 3). A resistance measurement circuit 443, as shown in FIG. 4D, may be employed to measure the resistance of the circuit to enable a determination of which cases 1, 2, or 3 is present. With SW1 and SW2 closed, the resistance may be measured. If the resistance is zero, there is an orientation resulting in one of the contacts 422b or 422c being in electrical contact with the connecting portion 442b (Case 2). The switches SW1 and SW2 may then be toggled by controls to open in sequence, one after another until the resistance becomes non-zero as measured by the resistance measurement circuit. The resistance measurement circuit may be any conventional electrical circuit for measuring resistance. This then ensures proper electrical connection to the electrodes 414, 430. Thus, in the case where the contacting member 437 is broken, the addition of an extra electrical contact 422c in contact with the contacting member 437, and a resistance measuring circuit may allow a positive electrical contact to be provided regardless of the rotational orientation. This routine may be run as a precursor to actually carrying out the analyte measurement by the main measurement system. The main measurement system will not be described further herein as it is conventional.

In another optional configuration, an insulating material layer may be applied over the connecting portion 442b in the region of intersection so that the contacting member 437 may be provided as a continuous unbroken ring.

Figure 4E:
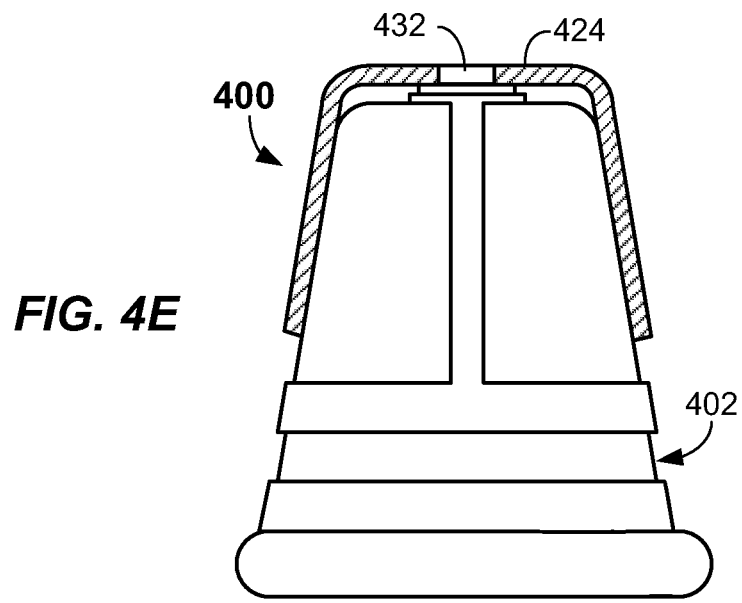
FIG. 4E is a partially cross-sectioned side view of another exemplary embodiment of an analyte sensor according to the present invention.

Furthermore, a cup-shaped second member 424, shown cross-sectioned in FIG. 4E, may be provided over the end of the base 402 which may allow for the inclusion of a capillary channel 432 for containing a bio-fluid sample. Other second member configurations may be utilized.

Figure 5C:
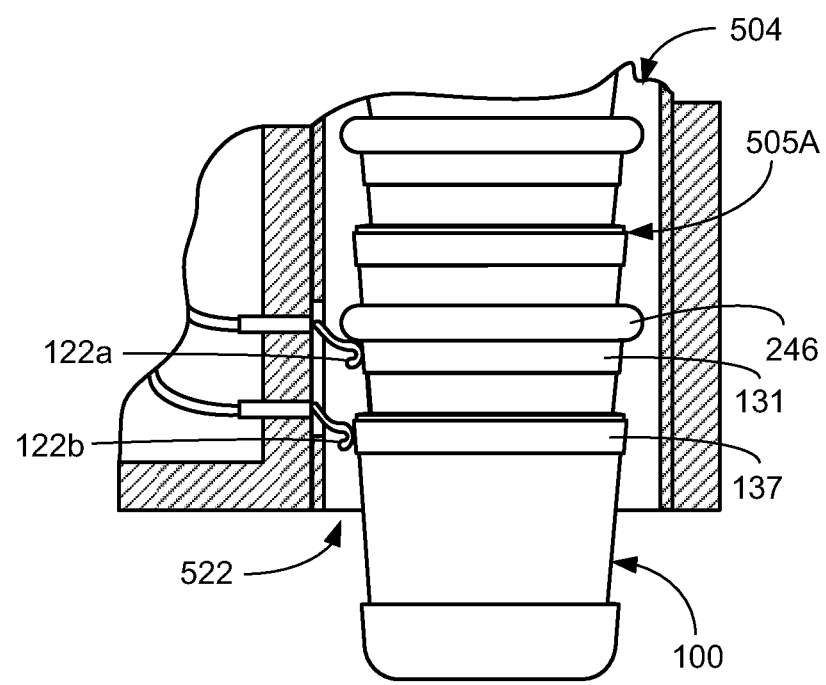
FIG. 5C is a partial cross-sectional view of a port of an analyte sensor dispenser system of FIG. 5A having a stack of analyte sensor therein.

FIGS. 5A-5C illustrate an exemplary embodiment of an analyte sensor dispenser system 500 according to an embodiment of the present invention. The system 500 includes a dispenser body 502 having a channel 504 extending within the dispenser body 502. The channel 504 may take on any suitable shape, such as curved path shown, or the straight path as shown in the FIG. 6C embodiment. The channel dimension should be slightly larger than a maximum diameter of the analyte sensor 100 dispensed therefrom. In some embodiments, the channel 504 may be a tube (e.g., a bent tube). A plurality of the analyte sensors 100, 400 described herein may be provided in a stacked configuration within the channel 504. For example, 5 or more, 10 or more, or even 15 or more analyte sensors 100 may be loaded into the channel 504 at a loading port 505. Optionally, a tube including a plurality of stacked analyte sensors 500A arranged in stacked configuration therein may be received (loaded) as a cartridge assembly within suitably-shaped molded recesses formed in respective halves of the body 502 such that the tube is retained therein. As heretofore described, each analyte sensor 100 includes at least one conductor, and preferably, a plurality of conductors formed thereon.

An advancing mechanism 506 may be coupled to at least one of the plurality of analyte sensors 100, and preferably to the stack of analyte sensors 500A and is adapted to cause movement of the sensor 100 and the stack 500A within the channel 504. The advancing mechanism 506 may include a pusher 508 such as a ball, a rod, or other contact component, which is adapted to contact an end of the last analyte sensor 500B in the stack of analyte sensors 500A. Utilizing the ball works well as a pusher 508 as the ball may minimize bind within the channel 504. In more detail, the advancing mechanism 506 may further include a cable 510 wound onto a reel 512, and a drive device 514 adapted to advance the cable 510 off from the reel 512. The cable 510 may be sufficiently rigid so that it may be advanced and not collapse/buckle when advancing the pusher 508. One implementation of the drive device 514 may include a gear 516 rigidly mounted to the reel 512 (e.g., formed integrally with), a ratchet arm 518 which engages the gear teeth of the gear 516, and a trigger 520 coupled to and adapted to advance the ratchet arm 518. One suitable trigger 520 may slide in a slot (not shown) formed in the body 502, for example. The ratchet arm 518 may be spring loaded (not shown) so that the ratchet arm 518 may engage the teeth of the gear 516 on an advancement stroke and skip over the teeth on a return stroke. A one-way clutch mechanism may be used, such as on another portion of the gear 516 to allow a detent to be provided during the advancement stroke, and stop rotation of the reel 512 during the return stroke. Other types of drive devices may be used, such as an electric drive motor.

In operation, as the advancing mechanism 506 is actuated by the user by displacing trigger 520 along a direction of the arrow shown, the reel 512 rotates about shaft 526 mounted in the halves of body 502 and individual analyte sensors 100 of the plurality of analyte sensors in the stack 500A are incrementally dispensed from a port 522 of the dispenser 500. As the analyte sensor 100 is at rest in the port 522 with the end of the analyte sensor 100 in an accessible position, the user may deposit a droplet of bio-fluid (e.g., blood) onto the end of the analyte sensor 100 so that it is drawn into the cavity 132 (FIG. 1C). Accordingly, a conventional analyte meter contained within the body 502 of the dispenser 500 may calculate and display an analyte concentration reading to the user on a digital display 524, for example. Electrical contacts 122a, 122b, as best shown in FIG. 5C, provided in the port 522 are adapted to contact the contacting portions 131, 137 of the first and second conductors 118, 136 (FIG. 1C) of the analyte sensor 100. The electrical contacts 122a, 122b may be coupled to (See FIG. 9) or extend through the wall of the channel 504, for example. As can be seen from FIG. 5C, the electrical contacts 122a, 122b may function as a detent mechanism to allow the sensor 100 to advance the stack 505A until the first electrical contact 122a rests against the lip 246 of the analyte sensor 100.

The dispenser body 502 may be a moldable plastic and formed in halves, for example. The channel 504 may be formed half in each of the halves of the body 502 or as a tube. The reel 512 and gear 516 may be mounted for rotation in the body 502 via the shaft 526 or the reel 512 may simply be received and rotatable in a pocket formed into one or more of the halves of the body 502.

Figure 6B:
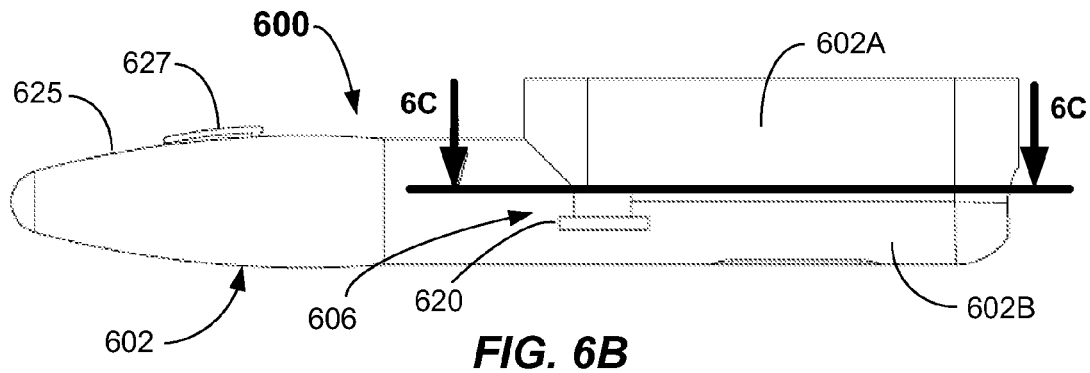
FIG. 6B is a side view of an analyte sensor dispenser system of FIG. 6A.
Figure 6C:
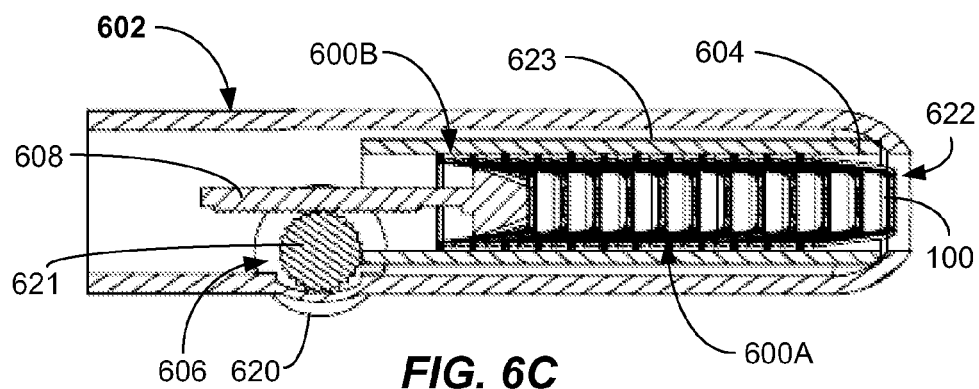
FIG. 6C is a partial, enlarged cross-sectional view of an analyte sensor dispenser system of FIG. 6B taken along section line 6C-6C.

FIGS. 6A-6C illustrates another exemplary embodiment of an analyte sensor dispenser system 600 according to an embodiment of the present invention. The system 600 includes a dispenser body 602, which may resemble a pen. The dispenser body 602 may include a straight channel 604 extending within the dispenser body 602, which is adapted to receive a stack of analyte sensors 600A. The stack of analyte sensors 600A may number, as in the previous embodiment, five or more, 10 or more, or even 15 or more analyte sensors 100. As heretofore described, each analyte sensor 100 may include at least one conductor, and preferably, a plurality of conductors formed thereon. As in the previous embodiment, an advancing mechanism 606 may be coupled to at least one of the plurality of analyte sensors 100, and preferably to the stack of analyte sensors 600A and is adapted to cause movement of the analyte sensor 100 and the stack 600A within the channel 604. The advancing mechanism 606 may advance the analyte sensors 100 incrementally as needed by the user.

As best shown in FIG. 6C, the advancing mechanism 606 may include a pusher 608 such as a rod, or other contact component, which is adapted to contact an end of the last analyte sensor 600B in the stack of analyte sensors 600A. In more detail, the advancing mechanism 606 may include a thumb wheel 620 mounted for rotation within the body 602. In some embodiments, the thumb wheel 620 may contact the pusher 608, such as along a side thereof, or a gear 621 coupled to or integral with the thumbwheel 620 so that rotation of the thumb wheel by a user will cause an advancement of the analyte sensor 100 out of a port 622. The movement of the pusher 608 may have a detent feature wherein advancements may be made in small, defined increments. Any suitable detent mechanism may be used, such as a detent (not shown) that engages the gear teeth of the gear 621.

Figure 9:
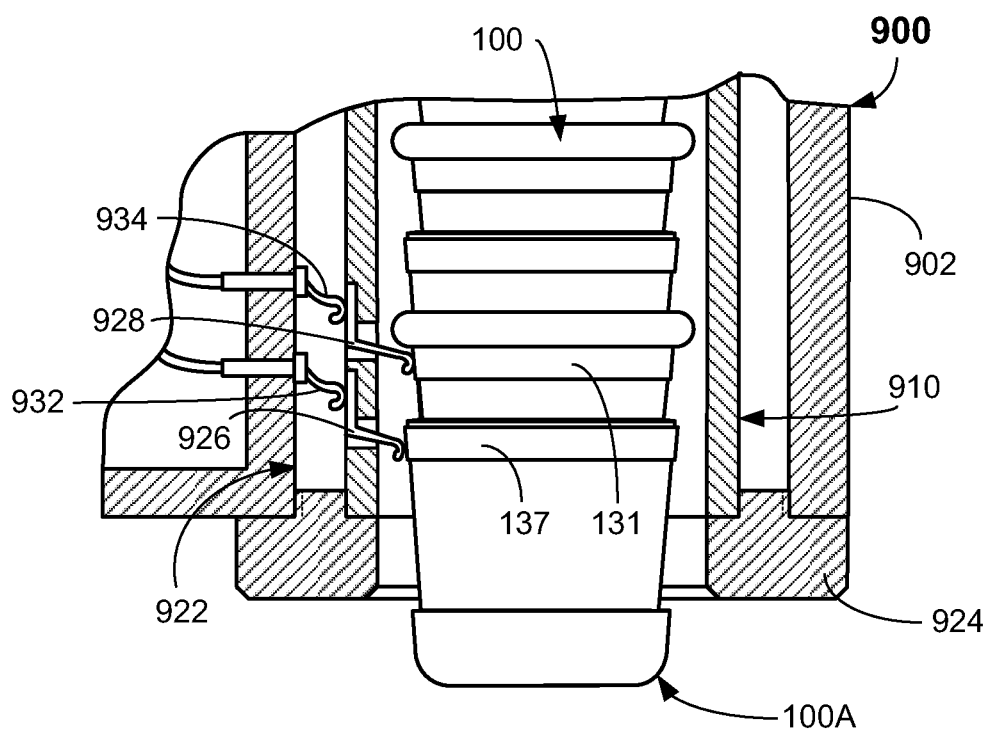
FIG. 9 is a partial cross-sectioned side view of an embodiment of cartridge assembly according to the present invention shown installed and received in an analyte meter.

As in the previous embodiment, electrical contacts may be provided in the port 622 which are adapted to contact the analyte sensor 100 when the sensor 100 is suitably positioned in the port 622 (e.g., at the end thereof) and ready for receiving a bio-fluid sample and carry out an analyte reading. The electrical contacts may be configured as shown in FIG. 5C or FIG. 9, for example. As such, the electrical contacts may provide for a detent feature, for example. The stack of sensors 600A may be loaded into the analyte sensor dispenser system 600 through the port 622 or otherwise loaded into the body 602, such as by having the top portion 602A of the body 602 hinge relative to the lower portion 602B. In the depicted embodiment, the stack of sensors 600A may be received in a tube 623. The stack of sensors 600A and tube 623 may make up a cartridge assembly that may be loaded into the body 602 as mentioned above. The analyte sensor dispenser system 600 may include, as in the previous embodiment, a digital display 624 for displaying the analyte reading to the user. The system 600 may include a cap 625, which may expose a lancet device of conventional construction adapted to receive disposable lancets, for example. A pocket clip 627 may be formed on the cap 625, for example.

Figure 7:
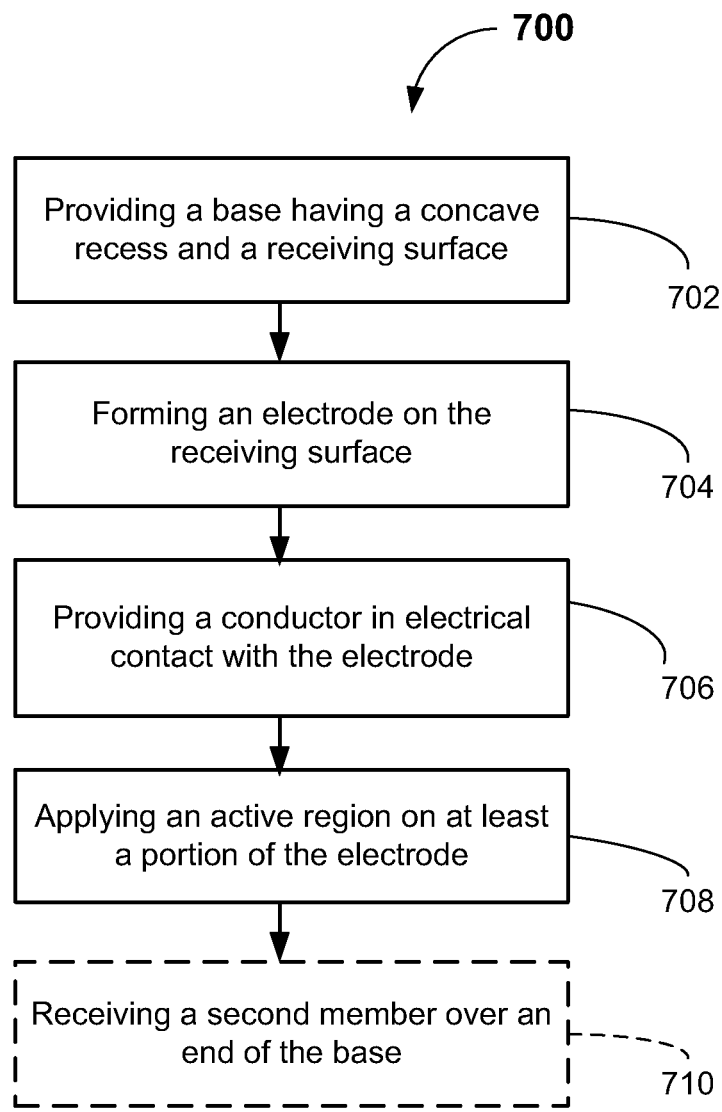
FIG. 7 is a flowchart illustrating methods of manufacturing the analyte sensors according to an embodiment of the present invention.
Figure 8:
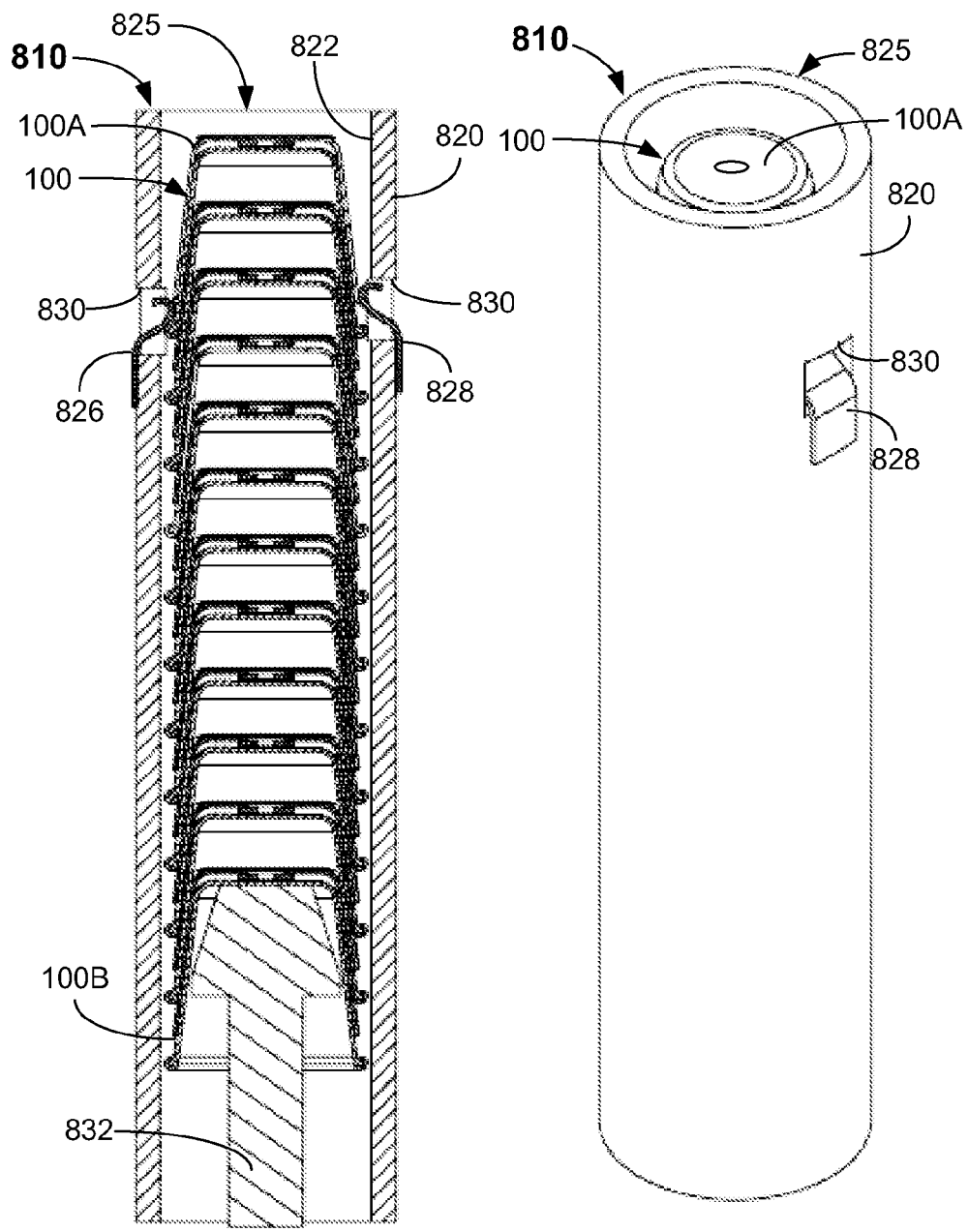
FIG. 8A is a cross-sectioned side view of an embodiment of a cartridge assembly according to the present invention.
FIG. 8B is an isometric view of the embodiment of cartridge assembly of FIG. 8A according to the present invention.

Methods for manufacturing embodiments of the analyte sensors 100, 400 of the invention will now be described with reference to FIG. 7. Methods of manufacturing analyte sensors 700 of the invention may comprise the steps of providing a base (e.g., a base 102 of insulating material) as in 702, the base having a first end (e.g., 104) and a second end (e.g., 106), and a first sidewall (e.g., 112) extending between the first end and the second end, the first end including a concave opening or recess (e.g., 108) and the second end including a receiving surface (e.g., 110); and forming a first electrode (e.g., 114) on the receiving surface in 704. An active region (e.g., 116) may be applied to be in contact with at least a portion of the first electrode in 708. A second electrode may also be formed adjacent to the first electrode, such as on the receiving surface as in the FIG. 4A embodiment, or otherwise in contact with the active region (e.g., 130). In these instances, the active region is provided in contact with at least a portion of the first and second electrodes. In the FIG. 1C embodiment, the second electrode (e.g., 130) is provided in contact with and opposite side of the active region (e.g., 116) than the first electrode (e.g., 114). In 706, a conductor (e.g., 118) may be provided in electrical contact with the first electrode. The conductor may be formed to include a contact portion (e.g., 131) adapted to be in electrical contact with a first electrical contact (e.g., 122a) of an analyte meter (see FIGS. 1C, 5C and 9).

In some embodiments, a second conductor (e.g., 136) may be provided in electrical contact with the second electrode. The second conductor may also extend along an outer surface of the sidewall. For example, in the FIG. 1C embodiment, the second conductor may extend along a sidewall of a second member (e.g., 124); the sidewall of the second member extending along the sidewall of the base. The conductors may extend down the same side or opposite sides of the base. In each embodiment herein, the electrical conductors may be formed to include a contact portion adapted to be in electrical contact with electrical contacts of an analyte meter. In some embodiments, a second member may be received over an end of the base in 710 and may be used to form a cavity adapted to receive a bio-fluid sample. In some embodiments, the second conductor may be formed on the second member, such as on an outside surface thereof. The second conductor including a contact portion formed thereon may be adapted to be in electrical contact with a second electrical contact of the analyte meter.

The electrodes and conductors may be made of any suitable electrically-conductive material and may be formed by any suitable method. For example, the electrodes and/or the conductors may be formed with a conductive ink using a screen printing, laser printing, or inkjet printing process, for example. Optionally, the electrodes and/or conductors may be formed by adhering a thin conductive film to the base and/or second member. The electrodes and conductors may be integrally formed, or formed as two components. They may be manufactured from the same or different materials.

In some embodiments, where a second member is provided over the end of the base, the second member may be provided and attached directly to the base, attached to the base via an adhesive layer, or attached to the base via any form of mechanical interference. Each of the base and the second member may be preformed or stamped out of a deformable polymer material. A hole may be provided in the second member (e.g., formed by cutting) for providing the cavity to promote capillary action of the bio-fluid sample, or to provide a recess for insertion of the conduction member as in the FIG. 1C embodiment.

FIGS. 8A and 8B illustrate a cross sectional view and an isometric view, respectively, of a cartridge assembly 810 according to another aspect of the present invention. The cartridge assembly 810 may interface with an analyte meter, such as a meter 600 shown in FIGS. 6A-6C. The cartridge assembly 810 may be appropriately configured so that the cartridge assembly 810 may be readily received into a meter and the sensors therein dispensed. Accordingly, when the cartridge assembly 810 is emptied, it may simply be replaced with a full cartridge. The cartridge assembly 810 may include a cartridge body 820, which may be a cylindrical tube for example, and which may include a channel 822 extending along a length thereof and adapted to receive a plurality of the analyte sensors 100 provided in a stacked orientation along the longitudinal length of the channel 822. Sensors 100 may be of any of the cup-shaped configurations described herein and may be stacked such that the walls of respective ones of the sensors 100 overlap each other and such that a seal is formed between an outer surface of one sensor 100 and the outside surface of the next adjacent sensor 100 in the stack. The channel 822 may be straight or slightly curved for example.

In operation, a first one of the sensors 100A of the plurality of sensors 100 stacked longitudinally in the channel 822 is provided in an end 825 of the channel 822 at an accessible position where the user may apply a bio-fluid sample to the electrochemically active region thereof. In the end position, the sensor 100A may be provided in electrical contact with electrical contacts 826, 828. The electrical contacts 826, 828 may be provided in the channel 822 in any suitable configuration, such as in an end thereof and on diametrically opposite sides thereof, as shown. Other configurations may be employed. Furthermore, the contacts 826, 828 may be spaced longitudinally at different longitudinal positions such that they may be appropriately positioned to be provided in electrical contact with the conductive contacting portions 131, 137 (FIG. 1C) of the end-positioned sensor 100A. The electrical contacts 826, 828 may pass through openings 830 in the cartridge body 820 and the portions of the contacts 826, 828 provided on an outer peripheral surface of the cartridge body 820 may be adapted to be received in electrical communication with engaging contacts in the meter. For example, contacts 122a, 122b, such as shown in FIG. 1C, may be configured to engage the electrical contacts 826, 828 upon insertion of the cartridge assembly 810 into a port of the meter. Thus, in operation, upon insertion of the cartridge 810 into the meter (e.g., 600 of FIG. 6A-6C), an electrical circuit may be created whereby electrical signals generated by use of the analyte sensor 100A may be received, processed and/or displayed by the meter (e.g., 600).

The cartridge assembly 810 may include a pushing member 832 such as a rod, puck, cylinder, or other contact component, which is adapted to contact a portion (e.g., an underside or end) of the last analyte sensor 100B in the stack of analyte sensors 100. In operation, the pushing member 832 may be contacted by any suitable advancing mechanism of the meter, such as a thumb-wheel advancing mechanism shown in FIG. 6A-6C or the mechanism shown in FIG. 5A-5B. Other suitable advancing mechanisms may be employed. Optionally, the contacting member may be part of the meter itself, and not part of the cartridge 810.

FIG. 9 illustrates another embodiment of cartridge assembly 910 installed into a port 922 of a meter 900. The cartridge assembly 910 may be received in the meter 900 and retained relative to a body 902 of the meter 900 by any suitable means. For example, the cartridge 910 may be received in the port 922 of the meter 900 and a threaded end cap 924 may be used to retain the cartridge 910 in place relative to the meter body 902. Optionally, a spring-loaded detent, slight interference fit, a latch or other locking mechanism may be used to retain the cartridge assembly 910 in the meter 900. When provided in the port 922, the contacts 926, 928 are provided in electrical contact with the contacting portions 131, 137 (FIG. 1C) of the end-most positioned sensor 100A. Likewise, contacts 932, 934 of the meter 900 may be provided in contact with contacts 926, 928 of the cartridge assembly 910 such that electrical connection to the processor (not shown) of the meter 900 may be accomplished. The cartridge assembly 910 may include a notch, tab or other alignment feature (not shown) for aligning the cartridge assembly 910 in the port 922 of the meter body 902 such that alignment of the contacts 926, 928 with contacts 932, 934 may be achieved.

The analyte sensors described herein may further include some form of underfill detection to determine whether a sufficient amount of the bio-fluid sample is present in the analyte sensor in order to provide an acceptable analyte concentration reading. For example, underfill detection may be provided by a method described in United States Application Publication 2009/0095071 to Wu et al. entitled "Underfill Detection System for a Biosensor." Described is a purely electrical solution wherein the method does not require the use of an additional electrode. Optionally, underfill detection may be provided by including an additional electrode. The additional electrode would be positioned at a radial outer extent of the active region so that when bio-fluid contact is made with the electrode, the presence of the bio-fluid sample at that position may be determined. The presence of the fluid at this outer radial location may indicate sufficient bio-fluid volume is present. Any suitable electrode construction may be employed.

The foregoing description discloses only exemplary embodiments of analyte sensors, apparatus including the same, and methods of manufacturing the sensors of the invention. Modifications of the above-disclosed analyte sensors, apparatus incorporating them, and methods for manufacturing them, which fall within the scope of the invention, will be readily apparent to those of ordinary skill in the art.

Accordingly, while the present invention has been disclosed in connection with exemplary embodiments thereof, it should be understood that other embodiments may fall within the spirit and scope of the invention, as defined by the following claims.

The invention claimed is:

1. An analyte sensor dispenser system, comprising:
    a dispenser body having a channel extending in the dispenser body;
    a plurality of cup-shaped analyte sensors each having a recess formed along the axial length thereof and arranged in a stacked configuration within the channel, each analyte sensor including at least one conductor;
    an advancing mechanism disposed within the dispenser body in contacting engagement with at least one of the plurality of analyte sensors;
    a port formed at a terminal end of the channel from which individual analyte sensors of the plurality of analyte sensors are incrementally dispensable; and
    at least one electrical contact disposed within the port adapted to provide electrical contact with the at least one conductor of each analyte sensor.

2. The analyte sensor dispenser system of claim 1, further comprising a first electrical contact and a second electrical contact disposed within the port for contact with a first conductor and a second conductor provided on the individual analyte sensor.

3. The analyte sensor dispenser system of claim 1, wherein the advancing mechanism further comprises a pusher component disposed in the channel to push an analyte sensor at a first end of the stacked configuration to advance the plurality of analyte sensors within the channel to the port.

4. The analyte sensor dispenser system of claim 3, wherein the advancing mechanism further comprises a drive device including a ratchet arm coupled to a reel rotatably mounted within the dispenser body, wherein the ratchet arm and the reel are coupled to the pusher component to advance the pusher component within the channel.

5. The analyte sensor dispenser system of claim 4, wherein the ratchet arm and the reel are coupled to the pusher component by a cable.

6. The analyte sensor dispenser system of claim 1, wherein the plurality of analyte sensors arranged in a stacked configuration within the channel are included within a cartridge assembly, wherein the cartridge assembly includes a cartridge body having an inner channel, wherein the plurality of analyte sensors are disposed within the inner channel.

* * * * *